United States Patent [19]

Monbaliu et al.

[11] Patent Number: 4,839,267

[45] Date of Patent: Jun. 13, 1989

[54] COLOUR PHOTOGRAPHIC MOTION PICTURE ELEMENT

[75] Inventors: Marcel J. Monbaliu, Mortsel; Paul L. Van Meerbeeck, Hulshout, both of Belgium

[73] Assignee: AGFA-Gevaert, N.V., Mortsel, Belgium

[21] Appl. No.: 110,798

[22] Filed: Oct. 21, 1987

[30] Foreign Application Priority Data

Nov. 21, 1986 [EP] European Pat. Off. ........ 86202066.6

[51] Int. Cl.$^4$ .................... G03C 1/38; G03C 7/34; G03C 7/24
[52] U.S. Cl. ................... 430/546; 430/140; 430/505; 430/552; 430/553; 430/944
[58] Field of Search ........... 430/140, 546, 944, 505, 430/552, 553

[56] References Cited

U.S. PATENT DOCUMENTS 3,912,515 10/1975 Nakajima et al. ............ 430/512
4,178,183 12/1979 Ciurca, Jr. et al. ............ 430/553
4,678,743 7/1987 Yamada et al. ............ 430/551
4,732,845 3/1988 Keiji et al. ............ 430/551

FOREIGN PATENT DOCUMENTS 0176628 4/1986 European Pat. Off. ............ 430/140

Primary Examiner—Paul R. Michl
Assistant Examiner—Lee C. Wright
Attorney, Agent, or Firm—A. W. Breiner

[57] ABSTRACT

Color photographic motion picture elements adapted to form a multicolor photographic dye image and an integral, infrared-absorbing, dye sound track and comprising a 1-hydroxy-2-N-(5-ballasted-thiazol-2-yl)-naphthamide coupler dispersed with the aid of a water-immiscible, high-boiling, oil-type hydrocarbon oil-former, said coupler bearing a phenyl group or a substituted phenyl group at the 4-position of the thiazol-2-yl ring and being capable of forming infrared-absorbing quinone imine dyes by reaction with an oxidized aromatic primary amino developing agent.

7 Claims, No Drawings

COLOUR PHOTOGRAPHIC MOTION PICTURE ELEMENT

DESCRIPTION

The present invention relates to colour photographic motion picture elements, adapted for forming a multicolour photographic dye image and an integral, infrared-absorbing, dye sound track, said elements comprising a novel coupler/oil-former combination, by which combination an improved integral, infrared-absorbing, dye sound track can be formed.

It is common practice nowadays to incorporate couplers into photographic silver halide emulsions by first dissolving them in oil-formers and dispersing the resulting coupler/oil-former droplets in the emulsions. Many classes of oil-formers have been described for that purpose. Reference can be made in this respect to the oil-formers listed in EP-A No. 0,176,628, which corresponds with U.S. Ser. No. 06/780,585, and to the oil-formers listed in the related literature mentioned therein. Other known oil-formers are i.a. the alkyl-substituted benzenes, the alkenes, and cycloalkenes described in GB-A No. 1,452,319 as high-boiling solvents for ultraviolet absorbers and couplers to be incorporated into common photosensitive silver halide materials. The vastness of the group of existing oil-formers is mainly due to the fact that many of them have an insufficient dissolving power towards couplers, which often leads to an unwanted crystallization and ineffective behaviour of the latter.

The photographic image as well as the sound track image in black-and-white motion picture projection films are known to consist of silver usually, the sound information in the sound track being present in the form of periodical variations in density or of periodical variations in the ratio between areas that are completely dark and areas that are fully bright. This sound information can be read optically by a photocell detecting infrared radiation that has been modulated by passing through these variations in density or in area. The photocells customarily used for this purpose are i.a. the S-1 photocells, which have a maximum sensitivity in the infrared region of the spectrum, more particularly in the infrared region from about 750 to about 850 nm, in which region silver absorbs uniformly.

Although in sound tracks of colour motion picture projection films silver has been used customarily, the application of silver therein requires special selective treatments including a separate development of the sound track portion. To avoid such special selective treatments attempts have been made to use dyes instead of silver for the sound tracks of colour motion picture projection films. This allows the formation of both a dye image and a dye sound track during the same and only colour development step. The dye that builds up the sound track is a quinone imine coupling product that should have peak absorption in the infrared region where the photocells, e.g. the S-1 photocells, are sensitive, namely from about 750 to about 850 nm.

Infrared-absorbing dyes that can be used at least partially in integral dye sound tracks have been disclosed in U.S. Pat. No. 2,266,452, U.S. Pat. No. 2,373,821, JP PU No. 59,838, GB-A No. 1,424,454, U.S. Pat. No. 3,458,315, U.S. Pat No. 3,476,563, GB-A No. 519,208, in Research Disclosure No. 13460 of June 1975, No. 15125 of November 1976, and No. 18732 of November 1979.

In U.S. Pat No. 4,178,183 the use of coupler/solvent particles in the formation of integral, infrared-absorbing, dye sound tracks in colour photographic motion picture elements has been described, the coupler being a 1-hydroxy-2-N-(4-phenyl-5-ballasted-thiazol-2-yl)-naphthamide and the solvent being a known oil-former like dibutyl phthalate. Unfortunately, the absorption peaks of the infrared-absorbing dyes formed thus far for integral dye sound tracks were not broad enough and were insufficiently bathochromic, so that silver was still needed at least partially to guarantee sufficient absorption in the sensitivity range of the S-1 photocells.

In the above-mentioned EP-A No. 0,176,628, which corresponds with the U.S. Ser. No. 06/780,585, a colour photographic motion picture element, adapted for forming a multicolour photographic dye image and an integral, infrared-absorbing, dye sound track has been disclosed, wherein use is made of at least one 1-hydroxy-2-N-(5-ballasted-thiazol-2-yl)-naphthamide coupler, the thiazol-2-yl group of which carries a 4-p-$C_1$-$C_4$alkoxyphenyl group or a 4-p-$C_1$-$C_4$alkylphenyl group. The coupler could be dispersed with the aid of a known oil-former like dibutyl phthalate or an oil-former of the class of the 1,3-dialkoxy-2-propanols and carboxylic, phosphoric, and phosphonic acid esters thereof. Notwithstanding the fact that the quinone imine dyes obtained from these modified 1-hydroxy-2-N-(5-ballasted-thiazol-2-yl)-naphthamide couplers have an enhanced infrared peak absorption and a more bathochromic absorption range, the density of the dye image obtained was sometimes still insufficient to dispense with a concurrent silver image.

It is an object of the present invention to provide colour photographic motion picture elements in which infrared-absorbing dyes for integral dye sound tracks can be formed without requiring special selective treatment as above referred to, the dye image obtained having sufficient density in the absence of silver.

This object is accomplished by the use, in colour photographic motion picture elements, adapted to form a multicolour photographic dye image and an integral, infrared-absorbing, dye sound track, of a 1-hydroxy-2-N-(5-ballasted-thiazol-2-yl)naphthamide coupler dispersed in said elements with the aid of at least one water-immiscible, high-boiling, oil-type hydrocarbon solvent or oil-former, said naphthamide coupler bearing a phenyl group or a substituted phenyl group at the 4-position of the thiazol-2-yl ring.

1-Hydroxy-2-N-(5-ballasted-thiazol-2-yl)-naphthamide couplers, which can be used advantageously in accordance with the present invention in combination with the above-mentioned, water-immiscible, high-boiling, hydrocarbon oil-type solvents or oil-formers, said couplers being synthesizable in a very simple and economic way, are those corresponding to the following general formula:

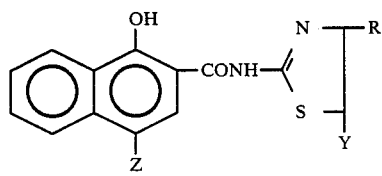

wherein

R—represents a phenyl group or a substituted phenyl group e.g. phenyl carrying at least one substituent selected from the group consisting of a halogen atom, cyano, cyclohexyl, alkylsulphonamido, an aryloxy group, an arylthio group, an alkyl group, an alkoxy group, an alkylthio group, an alkylcarbonyloxy group, the hydrogen atoms of said alkyl group, alkoxy group, alkylthio group, or alkylcarbonyloxy group being unsubstituted or at least one of them having been substituted by a halogen atom, Y—represents an alkyl group having at least 8 carbon atoms e.g. tetradecyl, which renders the coupler fast to diffusion in hydrophilic colloid media, Z—is hydrogen or a substituent, e.g. a chlorine or bromine atom, that splits off during the coupling reaction, thus conferring 2-equivalent character to the coupler, In addition to chlorine, other interesting substituents that may confer 2-equivalent character to the naphthamide couplers for use in accordance with the present invention are e.g. an acyloxy group, an alkoxy group, an aryloxy group, a heterocycloxy group, an alkylthio group, an arylthio group e.g. phenylthio and carboxyphenylthio, an alkylsulphonyl group, and arylsulphonyl group, and alkylsulphinyl group, an arylsulphinyl group, an alkyl- or aryl-substituted carbonylmethoxy group, an alkoxy- or aryloxy-substituted carbonylmethoxy group, and a heterocyclic thio group such as tetrazolylthio group.

Examples of substituents that can be carried by the phenyl group standing at the 4-position of the thiazol-2-yl ring are e.g. 2-methoxy, 4-methoxy, 4-ethoxy, 4-isopentyloxy, 4-methyl, 4-ethyl, 4-tert-butyl, 4-chloro, 4-difluoromethoxy, 3,4-dimethoxy, 4-phenoxy, and butylsulphonamido. Preferred substituents are 4-methoxy, 4-ethoxy, and 4-ethyl.

The present invention provides a photographic element comprising a support and a plurality of photosensitive silver halide emulsion layers for forming a multicolour photographic dye image and an integral, infrared-absorbing, dye sound track, one of said photosensitive silver halide emulsion layers or a non-photosensitive hydrophilic colloid layer in water-permeable relationship therewith comprising at least one dispersed 1-hydroxy-2-N-(5-ballasted-thiazol-2-yl)-naphthamide coupler capable of forming an infrared-absorbing quinone imine dye by reaction with an oxidized aromatic primary amino developing agent, said naphthamide coupler having been dispersed in said emulsion layer or in said colloid layer with the aid of at least one water-immiscible, high-boiling, oil-type solvent or oil-former, characterized in that said naphthamide coupler at the 4-position of its thiazol-2-yl ring bears a phenyl group or a substituted phenyl group and that said water-immiscible, high-boiling, oil-type solvent or oil-former is a hydrocarbon.

According to a preferred embodiment of the present invention the hydrocarbon oil-former comprised in said photographic element has been chosen from the group consisting of an alkane having at least 8 carbon atoms, an alkene having at least 8 carbon atoms, an alkyne having at least 8 carbon atoms, a cycloalkane, a cycloalkene, a polycyclic hydrocarbon, and an aromatic-aliphatic hydrocarbon.

According to one embodiment of the present invention a photographic element is provided, which comprises:
a support, an image-recording layer pack comprising in any desired sequence at least one image-recording blue-sensitive gelatin silver halide emulsion layer containing at least one yellow image dye-forming coupler, at least one image-recording red-sensitized gelatin silver halide emulsion layer containing at least one cyan image dye-forming coupler, at least one image-recording green-sensitized gelatin silver halide emulsion layer containing at least one magenta image dye-forming coupler, and one or more intermediate layers between said image-recording emulsion layers, a photosensitive sound-recording gelatin silver halide emulsion layer, and an antistress layer, said photosensitive sound-recording layer and/or a non-photosensitive hydrophilic colloid layer in water-permeable relationship therewith comprising a 1-hydroxy-2-N-(5-ballasted-thiazol-2-yl)-naphthamide coupler dispersed with the aid of at least one water-immiscible, high-boiling, hydrocarbon oil-type solvent or oil-former, said naphthamide coupler bearing a phenyl group or a substituted phenyl group at the 4-position of the thiazol-2-yl ring.

The present invention further also provides infrared-absorbing quinone imine dyes formed by a coupling reaction between an oxidized aromatic primary amino compound and a said 1-hydroxy-2-N-(5-ballasted-thiazol-2-yl)-naphthamide coupler dispersed with the aid of at least one water-immiscible, high-boiling, hydrocarbon oil-type solvent or oil-former.

Representative examples of 1-hydroxy-2-N-(5-ballasted-thiazol-2-yl)-naphthamide couplers that can be used in accordance with the present invention are listed in the following Table 1, the symbols used therein referring to the above general formula.

TABLE 1

| Coupler No. | R | Y | Z | Melting point °C. |
|---|---|---|---|---|
| 1 | phenyl | tetradecyl | chloro | 138 |
| 2 | phenyl | tetradecyl | hydrogen | 66 |
| 3 | 4-methoxyphenyl | tetradecyl | chloro | 138 |
| 4 | 4-methoxyphenyl | tetradecyl | bromo | 117 |
| 5 | 4-ethoxyphenyl | tetradecyl | chloro | 150 |
| 6 | 4-difluoromethoxyphenyl | tetradecyl | chloro | 143 |
| 7 | 4-methylphenyl | tetradecyl | chloro | 136 |
| 8 | 4-cyanophenyl | tetradecyl | chloro | 168 |
| 9 | 4-cyclohexylphenyl | tetradecyl | chloro | 130 |
| 10 | 4-butylsulphonylphenyl | tetradecyl | chloro | 160 |
| 11 | 4-phenylphenyl | tetradecyl | chloro | 156 |
| 12 | 3,4-dimethoxyphenyl | tetradecyl | chloro | 112 |
| 13 | 4-hexadecylphenyl | tetradecyl | chloro | 83 |
| 14 | 4-dodecylphenyl | tetradecyl | chloro | 74 |

The couplers for use in accordance with the present invention can be prepared by techniques well known to those skilled in the art e.g. according to the following general reaction scheme by first performing a cyclization reaction of appropriately substituted Alpha-bromoalkanoylbenzene derivatives with thiourea to form the corresponding 2-aminothiazoles and next to carry out a condensation of phenyl1-hydroxynaphthoates, which may carry a coupling off substituent in the 4-position, with these 2-aminothiazoles. In the following general reaction scheme, $R^1$ is hydrogen or one of the substituents, other than cyano, mentioned above that can be carried by the phenyl group, which will eventually stand at the 4-position of the thiazol-2-ring.

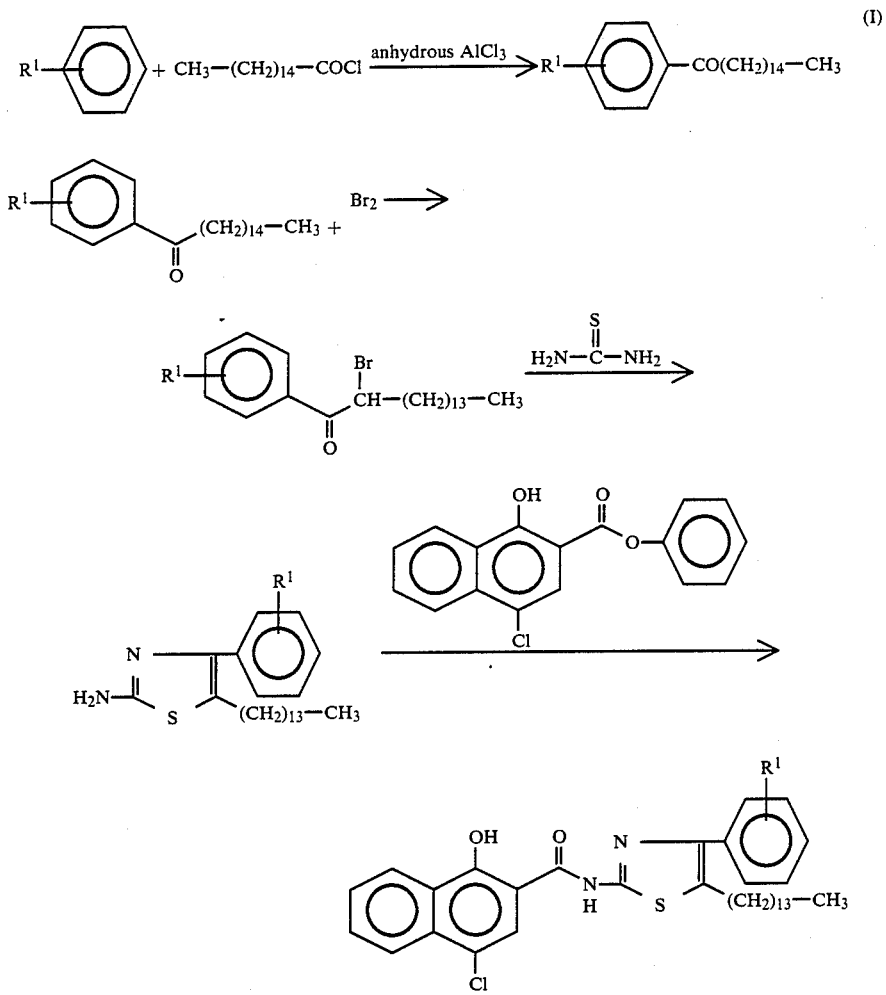

According to this reaction scheme the 1-hydroxy-2-N-(4-phenyl-5-tetradecyl-thiazol-2-yl)-4-chloro-naphthamide couplers corresponding to the above formula I can be prepared very simply and very economically.

In case $R^1$ is a p-cyano group, a direct Friedel-Crafts reaction as represented in the above reaction scheme is impossible. As a consequence, the starting product for coupler No. 8 is to be synthesized in another way as described in the following Preparation 1.

PREPARATION 1

A mixture of 59.3 g (0.15 mol) of 4-bromo-palmitophenone, 40.3 g of copper (I) cyanide (0.45 mol), and 300 ml of dimethylformamide is heated for 6 h at 150° C. The mixture is poured out in water. The precipitate is filtered with suction, dissolved in methylene chloride, and the inorganic salts formed are filtered off. The methylene chloride phase is concentrated by evaporation and the residue is recrystallized from ethanol.

Yield: 25 g of starting product for coupler No. 8.
Melting point: 72° C.

Examples of water-immiscible, high-boiling, oil-type hydrocarbon solvents or oil-formers that can be used in accordance with the present invention can be chosen from the following classes and representatives of hydrocarbons:

an alkane having at least 8 carbon atoms e.g. n-dodecane and n-hexadecane,
an alkene having at least 8 carbon atoms e.g. 1-nonene, 1-dodecene, 2,6-dimethyl-2,4,6-octatriene, and 1-hexadecene,
an alkyne having at least 8 carbon atoms e.g. 1-octyne,
a cycloalkane e.g. bicyclohexyl, tricyclo[5.2.1.0$^{2,6}$]decane, tercyclohexane, and cyclooctane,
an alkyl-substituted cyclohexane e.g. n-dodecycyclohexane, 2,4-dicyclohexyl-2-methyl-n-pentane, dicyclohexylmethane, p-n-dodecyl-bicyclohexyl, and butyl-tercyclohexane,
an alkenyl-substituted cyclohexane e.g. 1,2,4-trivinylcyclohexane,
a cycloalkene e.g. cyclooctene, cyclododecene, 1,5,9-cyclododecatriene, and limonene,
a polycyclic hydrocarbon e.g. decahydronaphthalene, and
an aromatic-aliphatic hydrocarbon e.g. dodecylbenzene and indan.

The water-immiscible, high-boiling, oil-type hydrocarbon solvents or oil-formers for use in accordance with the present invention can be prepared according to methods generally known by those skilled in the art.

Alkyl-substituted cyclohexanes can be synthesized as described in the following Preparation 2.

PREPARATION 2 n-dodecycyclohexane

An amount of 40 g of n-dodecylbenzene, 150 ml of ethanol, and 3 g of rhodium catalyst was placed in an autoclave. Hydrogenation was carried out for 3 h at a hydrogen pressure of 420 kPa and 50° C. The catalyst was filtered off and the filtrate was concentrated by evaporation. The residue was distilled under reduced pressure.

Yield: 40 g of n-dodecycyclohexane boiling at 118° C./0.5 mm.

The above-mentioned water-immiscible, high-boiling, oil-type hydrocarbons have been found to be efficient for dispersing the 1-hydroxy-2-N-(5-ballasted-thiazol-2-yl)-naphthamide couplers in photographic silver halide emulsions. It has also been found that upon storage of the photographic element comprising said coupler/oil-former combination, the dispersed coupler does not show any substantial tendency towards unwanted crystallization.

The surprising feature of the present invention is, however, that by the use of the coupler/oil-former combination according to the present invention in a colour photographic motion picture element the infrared-absorbing quinone imine dye image obtained therein by reaction with an oxidized aromatic primary amino developing agent has a substantially enhanced maximum density as compared with that obtained with known combinations of couplers and oil-formers in motion picture elements. Moreover, the quinone imine dyes formed in accordance with the present invention have a more bathochromic absorption than the quinone imine dyes formed according to known methods. The heat and light stability of the infrared-absorbing sound track dyes obtained with the coupler/oil-former combination used in accordance with the present invention is favourable and the loss in density of the dye tracks during ageing is low.

The 1-hydroxy-2-N-(5-ballasted-thiazol-2-yl)-naphthamide couplers corresponding to the above general formula I can be incorporated successfully into a hydrophilic colloid layer by dissolving them in a mixture of an auxiliary low-boiling water-immiscible solvent e.g. ethyl acetate and at least one water-immiscible, high-boiling, hydrocarbon oil-type solvent or oil-former, adding the resulting solution to an aqueous phase containing gelatin and a dispersing agent, passing the mixture through a homogenizing apparatus so that a dispersion of the oily coupler solution in an aqueous medium is formed, removing the auxiliary low-boiling water-immiscible solvent by evaporation, mixing the resulting dispersion with a hydrophilic colloid composition e.g. a gelatin silver halide emulsion, and coating the resulting composition in the usual manner.

The couplers according to the present invention can also be dispersed in hydrophilic colloid compositions with the aid of a combination of at least one hydrocarbon oil-former and at least one known oil-former e.g. an oil-former listed in the above-mentioned EP-A No. 0,176,628, which corresponds with the U.S. Ser. No. 06/780,585, or in the literature referred to therein.

For dispersing the 1-hydroxy-2-N-(5-ballasted-thiazol-2-yl)-naphthamide couplers the water-immiscible, high-boiling, hydrocarbon oil-type solvents or oil-formers can be used in widely varying concentrations e.g. in amounts ranging from about 0.1 to about 10 parts by weight and preferably from 0.5 to 2 parts by weight relative to the amount of the couplers dispersed therewith. Excellent results were obtained with 0.5 part by weight of the hydrocarbon oil-formers relative to 1 part of the couplers. For instance, very good results were obtained with a fine-grain silver halide sound-recording emulsion comprising per sq. m. an amount of silver that is equivalent with 0.6 g of silver nitrate, 0.8 g of 1-hydroxy-2-N-(5-ballasted-thiazol-2-yl)-naphthamide coupler, and 0.4 g of hydrocarbon oil-former.

Inasmuch as the nature and the concentration of the hydrocarbon oil-formers have an influence on the absorption characteristics of the quinone imine dyes obtained from the couplers according to the invention, it may thus be possible to adjust the absorption spectrum of these dyes in a desired sense to establishing the optimum oil-former composition and adjusting the concentration of said oil-formers.

It may be useful to combine at least one hydrocarbon oilformer with at least one auxiliary solvent that is insoluble or almost insoluble in water and has a boiling point of at most 150° C., such as lower alkyl acetates e.g. methyl acetate, ethyl acetate, n-propyl acetate, isopropyl acetate, butyl acetate, ethyl formiate, methyl propionate, ethyl propionate, carbon tetrachloride, sym-dichloroethylene, trichloroethylene, 1,2-dichloropropane, chloroform, amyl chloride, diethyl carbonate, diethyl ketone, methyl ethyl ketone, methyl-n-propylketone, diethyl ketone, diisopropyl ether, and nitromethane. The auxiliary solvent may also be a water-soluble organic solvent such as methanol, ethanol, isopropanol, dimethylsulphoxide, tetrahydrofuran, N-methylpyrrolidone, dioxan, acetone, butyrolactone, ethylene glycol, ethylene glycol monomethyl ether, ethylene glycol monoethyl ether, ethylene glycol monobutyl ether, diethylene glycol monoethyl ether, diethylene glycol monomethyl ether, glycerol, acetonitrile, formamide, dimethylformamide, tetrahydrothiophene dioxide, or dimethoxyethane. The auxiliary solvent may also be one described in i.a. U.S. Pat. Nos. 2,801,170; 2,801,171; 2,949,360; 2,835,579.

For processing the colour photographic motion picture elements for forming the image dyes as well as the infrared-absorbing dyes for integral dye sound tracks any conventional colour developing agent can be employed. Inasmuch as the colour developing agent will react in oxidized form with i.a the 1-hydroxy-2-N-(5-ballasted-thiazol-2-yl)-naphthamide couplers used in accordance with the present invention, the nature of the particular colour developing agent will, of course, also determine the characteristics of the infrared-absorbing dyes obtained therewith. Colour developing agents that are very well suited for processing the colour photographic motion picture elements comprising the coupler/oil-former combination according to the present invention are e.g. 2-amino-5-diethylamino-toluene hydrochloride, 2-amino-5-[N-ethyl-N-(methylsulphonylamino)-ethyl]-aminotoluene sulphate, 4-amino-3-methyl-N-ethyl-N-(Beta-hydroxyethyl)-aniline sulphate, and N,N-diethyl-p-phenylene diamine sulphate.

The colour photographic motion picture elements comprising the coupler/oil-former combination according to the present invention can be of the positive print film type or of the reversal film type.

Further details on the formation of integral infrared-absorbing sound tracks in photographic elements and on the infrared-absorbing quinone imine dyes obtained therewith as coupling product in a separate layer of such photographic elements during the same processing step as the one wherein the colour image is formed, can be found in U.S. Pat. Nos. 4,178,183; 4,233,389; 4,250,251; 4,430,422, in the above-mentioned EP-A No. 0,176,628, which corresponds with the U.S. Ser. No. 06/780,585, and in the Research Disclosures 18 732 (Nov. 1979) p. 634–638; 15 125 (Nov. 1976) p. 24–25; 13 460 (June 1975) p. 50.

Such sound-recording layer(s) should have a spectral or general sensitivity such that no undesired image is formed therein upon image-wise exposure of the image-recording layers.

The coupler/oil-former combination used in accordance with the present invention for forming infrared-absorbing quinone imine dyes is incorporated into a layer of the sound-recording layer unit making part of a colour photographic motion picture element. Such element may consist e.g. of a sound-recording layer unit comprising at least one sound-recording photosensitive gelatin silver halide emulsion layer coated on top of the image-recording layers.

A common layer composition of a colour photographic motion picture element comprises in order of sequence: a film support, the blue-sensitive silver halide emulsion layer(s) containing yellow-forming colour coupler(s), optionally (an) intermediate layer(s), the red-sensitized silver halide emulsion layer(s) containing cyan-forming colour coupler(s), optionally (an) intermediate layer(s), and the green-sensitized silver halide emulsion layer(s) containing magenta-forming colour coupler(s). The sound-recording layer(s) can have different locations as specified hereinafter, e.g. they can be coated on top of the green-sensitized layer(s).

Different sound-recording silver halide compositions are possible. For instance, the sound-recording silver halide emulsion is sensitive to ultraviolet radiation alone, or to infrared radiation, or to radiation of the spectral region between 470 to 500 nm. The important thing is that during the image exposure of the colour element the sound-recording layer does not respond. In these cases the sound-recording layer can be coated directly on the uppermost green-sensitized layer.

According to another alternative the sound-recording layer can be sensitive to the blue spectral region, but to a far less extent than the blue-sensitive layer(s) containing the yellow-forming couplers so that during the image exposure of the colour photographic motion picture element the sound-recording layer does not respond. The blue-sensitive sound-recording layer, which can e.g. be a fine-grain silver chlorobromide emulsion sensitive in the spectral range from 400 to 470 nm, may comprise a cyan-forming coupler in addition to the coupler forming an infrared-absorbing dye. When an additional cyan-forming coupler is used, the reaction with oxidized developer leads to the formation of a cyan dye in addition to the infrared-absorbing dye according to the invention. Cyan dyes are known to absorb also in the lower infrared region. The combined infrared absorption of both dyes thus increases the infrared absorption range and the density.

Likewise according to a further alternative the sound-recording layer can be sensitive to the green spectral region, but to a far less extent than the green-sensitized layer so that during the image exposure of the colour photographic motion picture element the sound-recording layer does not respond.

According to a further alternative the sound-recording layer can be sensitive to the red spectral region.

The sound-recording layer can be sensitive to both the red and green spectral regions, but to a far less extent than the image-recording red-sensitized and green-sensitized layer(s) so that during the image exposure of the colour photographic motion picture element the sound-recording layer does not respond.

According to all these above-mentioned embodiments the sound-recording layer contains a coupler/oil-former combination according to the present invention for forming infrared-absorbing dye sound tracks.

According to a further embodiment the colour photographic motion picture element comprises in order of sequence: a film support, the blue-sensitive silver halide emulsion layer(s) containing yellow-forming colour coupler(s), optionally (an) intermediate layer(s), the red-sensitized silver halide emulsion layer(s) containing cyan-forming colour coupler(s), optionally (an) intermediate layer(s), the sound-recording silver halide emulsion layer(s) containing a coupler/oil-former combination according to the present invention for forming infrared-absorbing dye(s), optionally (an) intermediate layer(s), the green-sensitized silver halide emulsion layer(s) containing magenta-forming colour couplers, and if desired (an) antistress layer(s). According to this embodiment the sound-recording silver halide emulsion layer(s) containing a coupler/oil-former combination according to the present invention is (are) sensitive in the blue spectral region from 400 to 470 nm, but is (are) far less sensitive than the blue-sensitive silver halide emulsion layer(s), and it (they) may contain in addition to the coupler/oil-former combination (a) cyan-forming colour coupler(s) as already described above. The silver halide of this (these) sound-recording emulsion layer(s) may be silver chloride or chlorobromide, preferably fine-grain silver chloride comprising 0–40 mol% bromide and 0–5 mol% iodide.

According to a different embodiment the colour photographic motion picture element does not encompass a separate sound-recording layer containing a coupler-/oil-former combination according to the present invention. Instead thereof the coupler/oil-former combination according to the present invention can be incorporated e.g. together with magenta-forming coupler(s) into the green-sensitized layer(s). However, the coupling speed of the magenta-forming couplers should then substantially exceed the coupling speed of the couplers forming the sound track dyes, so that in case of a normal image-wise exposure, the latter couplers, which are slow-coupling, cannot be affected as a result of insufficient amounts of oxidized developer. During the intensive sound track exposure both kinds of couplers respond and form their respective dyes, but the S-1 photocells only react to the infrared density obtained. Alternatively, the couplers that are capable of forming infrared-absorbing dyes can be incorporated together with the cyan image-forming coupler(s) into the red-sensitized layer(s). During the intensive sound track exposure both kinds of couplers respond and form their respective dyes, but the S-1 photocells again only react to the infrared density obtained.

In all above-mentioned embodiments the uppermost emulsion layer may, of course, be protected by (an) antistress layer(s).

Further details on layer structures of colour photographic motion picture elements can be found in U.S. Pat. Nos. 3,705,799, 3,705,801, 3,737,312, and 4,208,210; in DE-A No. 2,302,661; in GB-A Nos. 1,411,311, 1,429,108, and in the Research Disclosure 18 732 (November 79) p. 634–38.

Although in the making of dispersions of the coupler-/oil-former combination according to the present invention in hydrophilic colloid compositions gelatin is favoured as hydrophilic colloid, other water-soluble colloidal substances or mixtures of these can be used too e.g. colloidal albumin, starch, zein, alginic acid and derivatives thereof, such as salts, esters, and amides, casein, cellulose derivatives such as carboxymethyl cellulose, synthetic hydrophilic colloids such as polyvinyl alcohol, poly-N-vinyl pyrrolidone, anionic polyurethans, copolymers of acrylic esters, acrylonitrile, and acrylamides, etc.

During the manufacture of the colour photographic silver halide motion picture element according to the invention, the couplers corresponding to the above general formula I can be incorporated in the presence of at least one of the above defined hydrocarbon oil-formers into the coating composition of the silver halide emulsion layer(s) or other colloid layer(s) in water-permeable relationship therewith according to any technique known by those skilled in the art of incorporating couplers, into colloid compositions. For more details about particularly suitable techniques that can be employed for dispersing the couplers of the invention into hydrophilic colloid compositions there can be referred to U.S. Nos. 2,304,939; 2,304,940; 2,322,027; 2,801,170; 2,801,771; and 2,949,360.

The couplers corresponding to the above general formula I can be dispersed in the presence of a surface-active agent or dispersing aid. The surface-active agent used may be of the ionic, non-ionic or amphoteric type. Examples of suitable ionic surface-active agents are the sodium salt of oleylmethyltauride, sodium stearate, 2-heptadecyl-benzimidazole-5-sulphonic acid sodium salt, sodium sulphates of aliphatic alcohols containing more than 5 carbon atoms per molecule, e.g. 2-methylhexanol sodium sulphate; the sodium salt of di-isooctyl ester of sulphonated succinic acid, sodium dodecyl sulphate and p-dodecylbenzene sulphonic acid sodium salt. Examples of suitable non-ionic surface-active agents are saponine, condensation products of ethylene oxide and alkyl phenols, e.g. p-octylphenol and p-isononyl phenol and phenylethylene glycol oleate. Other examples of anionic and non-ionic surface-active agents can be found in GB-A No. 1,460,894.

A survey of surface-active agents, representatives of which can be used in dispersing the couplers corresponding to the above general formula, was made by Gerhard Gawalek in "Wasch- und Netzmittel" Akademieverlag, Berlin (1962).

It is also possible to use mixtures of anionic and non-ionic surface-active agents as described e.g. in GB-A No. 1,460,894.

Other interesting surface-active agents that can be used in dispersing the coupler/oil-former combination according to the present invention are the short-chain fluorine-containing surface-active agents disclosed in U.S. No. 4,292,402.

The photosensitive silver halide emulsions used in the making of colour photographic motion picture elements according to the present invention can be sensitized chemically as well as optically. They can be sensitized chemically by carrying out the ripening in the presence of small amounts of sulphur-containing compounds such as allyl thiocyanate, allyl thiourea, or sodium thiosulphate. The emulsions can also be sensitized by means of reducing agents e.g. tin compounds as described in FR-A No. 1,146,955 and in BE-A No. 568,687, iminoaminomethane sulphinic acid compounds as described in GB-A No. 789,823 and small amounts of noble metal compounds such as gold, platinum, palladium, iridium, ruthenium, and rhodium compounds. They can be sensitized optically by means of cyanine and merocyanine dyes.

The emulsions can also comprise compounds that sensitize the emulsions by development acceleration e.g. compounds of the polyoxyalkylene type such as alkylene oxide condensation products as described i.a. in U.S. Pat. Nos. 2,531,832, 2,533,990, in GB-A Nos. 920,637; 940,051; 945,340; 991,608 and 1,091,705, onium derivatives of amino-N-oxides as described in GB-A No. 1,121,696, and thioethers as described in U.S. Pat. No. 4,292,400.

Further, the emulsions may comprise stabilizers e.g. heterocyclic nitrogen-containing thioxo compounds such as benzothiazoline-2-thione and 1-phenyl-2tetrazoline-5-thione and compounds of the hydroxytriazolopyrimidine type. They can also be stabilized with an aromatic or heterocyclic mercapto compound as described in the GB-A No. 39457/80 or with mercury compounds such as the mercury compounds described in BE-A Nos. 524,121; 677,337, and in GB-A No. 1,173,609.

The photosensitive emulsions containing the coupler-/oil-former combination according to the present invention may also comprise any other kind of ingredient such as those described for such emulsions in Research Disclosure no. 17,643 of December 1978.

The emulsions can be coated on a wide variety of photographic emulsion supports. Typical supports include cellulose ester film, polyvinylacetal film, polystyrene film, polyethylene terephthalate film and related films or resinous materials.

The infrared-absorbing quinone imine dyes formed by a coupling reaction of 1-hydroxy-2-N-(5-ballasted thiazol-2-yl)-naphthamide couplers corresponding to the above general formula I with an oxidized aromatic primary amino compound can be used also as filter dyes in non-photographic materials such as in glass or synthetic resin materials e.g. in window glass as commonly used in shop and office windows for filtering the sun rays. It is obvious that the infrared-absorbing dyes obtained in accordance with the invention may find other interesting applications.

The following examples illustrate the present invention.

EXAMPLE 1

A colour photographic motion picture element having the following layer sequence was made:
black antihalation layer,
transparent film support,
subbing layer,
image-recording blue-sensitive gelatin silver halide emulsion layer containing a yellow image dye-forming coupler,
gelatin intermediate layer,
image-recording red-sensitive gelatin silver halide emulsion layer containing a cyan image dye-forming coupler,
sound-recording fine-grain gelatin silver chlorobromide emulsion layer sensitive in the blue spectral region from 400 to 470 nm and comprising silver in an amount equivalent to 0.6 g of silver nitrate per sq. m., 1.5 g/sq. m. of gelatin and 0.75 g/sq. m. of 1-hydroxy- 2-N(4-p-methoxyphenyl-5-tetradecyl-thiazol-2-yl)-4-chloro-naphthamide (Coupler 3 of Table 1), dispersed with the aid of n-dodecane in an amount of 0.5 parts by weight on the amount of naphthamide coupler, image-recording green-sensitized gelatin silver halide emulsion layer containing a magenta image dye-forming coupler, antistress layer.

The colour photographic motion picture element was exposed to white light having a colour temperature of 3200°K, to be recorded in the image-recording layers and then exposed again in the sound track area to light so as to affect the sound-recording layer.

The exposed element was processed, no special selective treatment being given to the sound-recording layer. The processing was as follows: The element was rinsed for 15 s in a prebath at 27° C. having the following composition:

| water | 800 ml |
| borax | 20 g |
| anhydrous sodium sulphate | 100 g |
| sodium hydroxide | 1 g |
| water to make | 1000 ml |
| | (pH 9.25 at 27° C.) |

The black antihalation layer was removed with water at 27° C. Next, the element was immersed for 3 min in a colour developing bath at 36.7° C. (±0.1) having the following composition:

| water | 800 ml |
| calcium-sequestering agent | 1 ml |
| anhydrous sodium sulphite | 4.35 g |
| 2-amino-5-diethylamino-toluene hydrochloride | 2.95 ml |
| anhydrous sodium carbonate | 17.10 g |
| anhydrous sodium bromide | 1.72 g |
| 7 N sulphuric acid | 0.62 ml |
| water to make | 1000 ml |
| | (pH 10.53 at 27° C.) |

The element was treated with the following stopbath for 40 s at 27° C.:

| water | 900 ml |
| 7 N sulphuric acid | 50 ml |
| water to make | 1000 ml |
| | (pH 0.9 at 27° C.) |

Next, the element was bleached in the following bath for 1 min at 27° C.:

| water | 900 ml |
| anhydrous potassium hexacyanoferrate (III) | 30 g |
| anhydrous sodium bromide | 17 g |
| water to make | 1000 ml |
| | (pH 6.5 at 27° C.) |

The bleached element was rinsed in water for 40 s at 27° C. and next immersed in the following fixing bath for 40 s at 27° C.:

| water | 800 ml |
| 58% aqueous solution of ammonium thiosulphate | 100 ml |
| anhydrous sodium sulphite | 2.50 g |
| anhydrous sodium hydrogen sulphite | 10.30 g |

-continued

| water to make | 1000 ml |
| | (pH 5.8 at 27° C.) |

Finally, the element was rinsed for 1 min in water at 27° C., immersed for 10 s in the following stabilizing bath at 27° C., and allowed to dry:

| water | 900 ml |
| 37.5% aqueous solution of formaldehyde | 15 ml |
| stabilizer additive | 0.14 ml |
| water to make | 1000 ml. |

As a consequence of the high standards reached with the coupler/oil-former combinations of the present invention, it is possible to use an image- and sound-recording colour photographic motion picture element in which the sound record is processed simultaneously with the image record using the same baths, the sound record entirely consisting of an infrared-absorbing quinone imine dye having an enhanced maximum density as compared with that obtained with known combinations of couplers and oil-formers. In fact, the maximum density obtained according to the present invention, was sufficiently high as to make it possible to dispense with the hitherto necessary concurrent silver image in dye sound tracks.

The heat and light stability of the quinone imine dyes obtained in accordance with the present invention is favourable and the loss in density of the dye tracks during ageing is very low.

Comparable results were obtained with the other couplers listed in Table 1.

EXAMPLE 2

In order to facilitate evaluation of the quinone imine dye sound tracks formed, samples were prepared of photographic elements as described in Example 1 with the difference than no image-recording layers were coated onto the subbed film support and that the nature and the amount of the oil-former in the sound-recording layer was as specified in Table 2 hereinafter.

One sample incorporated the generally known oil-former dibutyl phthalate (in Table 2 identified as oil-former A) in the sound-recording layer, a second sample incorporated the 2-ethylhexanoic acid ester of 1-n-butoxy-3-(2'-ethyl)-n-hexyloxy-2-propanol (in Table 2 identified as oil-former B), and a third sample incorporated the myristic acid ester of 1-methoxy-2-propanol (in Table 2 identified as oil-former C), both latter oil-formers being described in the above-mentioned EP-A No. 0,176,628, which corresponds with the U.S. Ser. No. 06/780,585. These three samples were entered in the test for comparison purposes.

The samples were exposed through a step wedge having a constant of 0.5, the density steps of which range from density 0.5 at step 1 to density 3 at step 6, to light so as to affect the sound-recording layers. The samples were then processed as described hereinbefore for the multilayer colour photographic motion picture elements containing image-recording layers also.

In Table 2 the amount of oil-former is specified in parts by weight calculated on the weight of the 1-hydroxy-2-N-(4-p-methoxyphenyl-5-tetradecyl-thiazol-2-yl)-4-chloro-naphthamide coupler dispersed therewith in the sound-recording layer. The results given in Table 2 for maximum density (D max) and peak absorption (Lambda max) were measured at step 2.

TABLE 2

| Oil-former | parts by weight | D max | Lambda max in nm |
|---|---|---|---|
| A (Comparison) | 0.5 | 1.01 | 860 |
| B (Comparison) | 0.5 | 1.22 | 870 |
| C (Comparison) | 0.5 | 1.38 | 868 |
| 1-hexadecene | 0.5 | 1.78 | 880 |
| n-dodecane | 0.5 | 1.90 | 880 |
| dicyclohexylmethane | 0.5 | 1.88 | 874 |
| dicyclohexyl | 0.25 | 1.63 | 870 |
| dicyclohexyl + 4-tercyclohexane | each 0.25 | 1.75 | 874 |

The above results show that the maximum density reached by means of the coupler/oil-former combinations in sound-recording layers of colour photographic motion picture elements according to the present invention, in other words the combinations with at least one hydrocarbon as oil-former, is considerably higher than the maximum density obtained by means of coupler/oil-former combinations with the oil-formers B and C according to the above-mentioned EP-A No. 0,176,628 and drastically higher than the maximum density obtained by means of the coupler/oil-former combination in which the oil-former is the generally known dibutyl phthalate (oil-former A).

Moreover, the results obtained for peak absorption show that the quinone imine dyes formed in accordance with the present invention have an infrared absorption range that is shifted bathochromically as compared with that of the quinone imine dyes formed according to known methods (A, B, and C). In this respect it is to be pointed out that the peak absorption of only 870 nm obtained with dicyclohexyl is due to its halved amount. Yet, the maximum density obtained with this halved amount of dicyclohexyl is markedly higher than that obtained with the oil-formers A, B, and C.

EXAMPLE 3

Samples of sound-recording layers on subbed film supports were made as described in Example 2. The samples were identical except for the nature of the coupler and of the oil-former. All samples comprised Coupler No. 2 of Table 1, which has been described in the above-mentioned U.S. Pat. No. 4,178,183. The oil-former 2,4-di-tert-pentylphenol, also described in the latter document, was chosen for comparison with hydrocarbon oil-formers. In each sample the oil-former was present in an amount of 50% by weight calculated on the weight of Coupler No. 2.

The samples were exposed and processed as described in Example 1.

The results given in Table 3 for maximum density (D max) and peak absorption (Lambda max) were measured at step 3.

TABLE 3

| Oil-former | D max | Lambda max in nm |
|---|---|---|
| 2,4-di-tert-pentylphenol (Comparison) | 1.68 | 730 |
| dicyclohexyl | 2.00 | 800 |
| n-dodecylcyclohexane | 1.94 | 806 |
| n-hexadecane | 1.91 | 800 |

The above results show that the maximum density obtained with Coupler No. 2 (described in the above-mentioned U.S. Pat. No. 4,178,183), being dispersed with the aid of hydrocarbon oil-formers in accordance with the present invention, by far exceeds the maximum density obtained with the combination of the same coupler and the oil-former 2,4-di-tert-pentylphenol according to the above-mentioned U.S. Pat. No.4,178,183.

The peak absorption of the quinone imine dyes formed in accordance with the present invention is shifted bathochromically as compared with that of the quinone imine dye obtained from the comparison sample.

EXAMPLE 4

Samples of sound-recording layers on subbed film supports were made as described in Example 2. The samples were identical except for the nature of the coupler and of the oil-former. In each sample the oil-former was present in an amount of 50% by weight calculated on the weight of the coupler.

The samples were exposed and processed in the same way as described in Example 1, except that instead of 2-amino-5-diethylamino-toluene hydrochloride colour developing agent 2-amino-5-[N-ethyl-N-(methylsulphonylamino)-ethyl]-aminotoluene sulphate was used. It is to be noted also that in the latter development a higher dose is required to achieve the same density values as in the first development.

The results of maximum density (D max) and peak absorption (Lambda max) were measured at steps 3 or 4 as indicated in Table 4. The oil-former C listed in Table 4 is the myristic acid ester of 1-methoxy-2-propanol described in the above-mentioned EP-A No. 0,176,628, which corresponds with the U.S. Ser. No. 06/780,585.

TABLE 4

| Coupler No. | Oil-former | Step | D max | Lambda max in nm |
|---|---|---|---|---|
| 8 | C | 3 | 0.76 | 700 |
| 8 | n-dodecylbenzene | 3 | 2.00 | 868 |
| 9 | C | 4 | 1.64 | 850 |
| 9 | n-dodecylbenzene | 4 | 2.94 | 860 |

The above results show that the maximum density obtained with Couplers 8 and 9, being dispersed with the aid of the hydrocarbon oil-former in accordance with the present invention, by far exceeds the maximum density obtained with the combination of the same couplers and the oil-former C described in the above-mentioned EP-A No. 0,176,628, which corresponds with the U.S. Ser. No. 06/780,585 US.

Moreover, the peak absorption of the quinone imine dyes formed in accordance with the present invention is found to be shifted bathochromically as compared with that of the quinone imine dye obtained in the presence of the known oil-former C.

Comparable results were obtained with the other couplers of the present invention.

We claim:

1. Photographic element comprising a support and a plurality of photosensitive silver halide emulsion layers for forming a multicolour photographic dye image and an integral, infrared-absorbing, dye sound track, one of said photosensitive silver halide emulsion layers or a non-photosensitive hydrophilic colloid layer in water-permeable relationship therewith comprising at least one dispersed 1-hydroxy-2-N-(5-ballasted-thiazol-2-yl)-naphthamide coupler capable of forming an infrared-absorbing quinone imine dye by reaction with an oxidized aromatic primary amino developing agent, said naphthamide coupler having been dispersed in said emulsion layer or in said colloid layer with the aid of at least one water-immiscible, high-boiling, oil-type solvent or oil-former, wherein said naphthamide coupler at the 4-position of its thiazol-2-yl ring bears a phenyl group and said water-immiscible, high-boiling, oil-type solvent or oil-former is a hydrocarbon.

2. A photographic element according to claim 1, wherein said hydrocarbon has been chosen from the group consisting of an alkane having at least 8 carbon atoms, an alkene having at least 8 carbon atoms, an alkyne having at least 8 carbon atoms, a cycloalkane, a cycloalkene, a polycyclic hydrocarbon, and an aromatic-aliphatic hydrocarbon.

3. A photographic element according to claim 1, wherein said 1-hydroxy-2-N-(5-ballasted-thiazol-2-yl)-naphthamide coupler corresponds to the following general formula I:

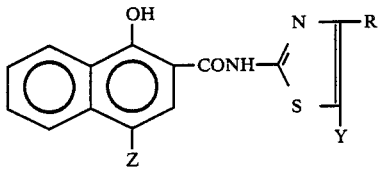

wherein:
R—represents a phenyl group,
Y—represents an alkyl group having at least 8 carbon atoms, which renders the coupler fast to diffusion in hydrophilic colloid media,
Z—is hydrogen or a substituent that splits off during the coupling reaction, thus conferring 2-equivalent character to the coupler, 4. A photographic element according to claim 3, wherein R is 4-methoxyphenyl, 4-ethoxyphenyl, or 4-ethylphenyl, Y is tetradecyl, and Z is chloro.

5. A photographic element according to claim 1, comprising:
a support,
an image-recording layer pack comprising in any desired sequence at least one image-recording blue-sensitive gelatin silver halide emulsion layer containing at least one yellow image dye-forming coupler, at least one image-recording red-sensitized gelatin silver halide emulsion layer containing at least one cyan image dye-forming coupler, at least one image-recording green-sensitized gelatin silver halide emulsion layer containing at least one magenta image dye-forming coupler, and one or more intermediate layers between said image-recording emulsion layers,
a photosensitive sound-recording gelatin silver halide emulsion layer, and
an antistress layer,
wherein said photosensitive sound-recording layer and/or a non-photosensitive hydrophilic colloid layer in water-permeable relationship therewith comprises a 1-hydroxy-2-N-(5-ballasted-thiazol-2-yl)-naphthamide coupler dispersed with the aid of at least one water-immiscible, high-boiling, hydrocarbon oil-type solvent or oil-former, said naphthamide coupler bearing a phenyl group at the 4-position of the thiazol-2-yl ring.

6. A photographic element according to claim 1, wherein said naphthamide coupler has been dispersed in one of said photosensitive silver halide emulsion layers or in said non-photosensitive hydrophilic colloid layer in water-permeable relation- ship therewith with the aid of n-dodecane, 1-hexadecene, or bicyclohexyl.

7. A photographic element according to claim 1, wherein said oil-former is used in amounts ranging from 0.5 to 2 parts by weight relative to the amount of said 1-hydroxy-2-N-(5-ballasted-thiazol-2-yl)-naphthamide coupler dispersed therewith.

* * * * *